US010682101B2

(12) United States Patent
Glode et al.

(10) Patent No.: US 10,682,101 B2
(45) Date of Patent: Jun. 16, 2020

(54) TECHNIQUES FOR RETRIEVING PERFORMANCE DATA FROM AN EXERCISE DATABASE

(71) Applicant: Under Armour, Inc., Baltimore, MD (US)

(72) Inventors: Christopher Glode, Denver, CO (US); Abhi Bhatt, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 459 days.

(21) Appl. No.: 14/937,059

(22) Filed: Nov. 10, 2015

(65) Prior Publication Data

US 2017/0128777 A1 May 11, 2017

(51) Int. Cl.

*A61B 5/00* (2006.01)
*G09B 19/00* (2006.01)
*G16H 50/30* (2018.01)
*G16H 20/30* (2018.01)

(52) U.S. Cl.

CPC .......... *A61B 5/7278* (2013.01); *G09B 19/003* (2013.01); *G09B 19/0038* (2013.01); *G16H 20/30* (2018.01); *G16H 50/30* (2018.01)

(58) Field of Classification Search

None

See application file for complete search history.

(56) References Cited

U.S. PATENT DOCUMENTS

2002/0165443 A1* 11/2002 Mori .................... A61B 5/0002 600/407
2008/0004834 A1* 1/2008 Sugai .................. G01C 22/006 702/160
2008/0155077 A1* 6/2008 James ................ G06F 19/3406 709/223
2010/0292600 A1* 11/2010 DiBenedetto ...... A63B 24/0062 600/520
2013/0217979 A1* 8/2013 Blackadar ........... A61B 5/0024 600/301

* cited by examiner

*Primary Examiner* — Bruk A Gebremichael

(74) *Attorney, Agent, or Firm* — Maginot, Moore & Beck LLP

(57) ABSTRACT

Techniques are provided for retrieving performance data from an exercise database. At a server device, data entries are stored in a database. Each of the exercise data entries comprises one or more performance metrics for a corresponding metric category. The server receives first performance data of an individual performing an exercise event and selects one of the exercise entries in the database as a selected exercise entry. The server determines a metric category for the first performance data and matches the metric category of the first performance data with a same metric category for the selected exercise entry. The server retrieves second performance data from the selected exercise data entry. The second performance data belongs to a metric category that does not match the metric category of the first performance data. The server assigns the second performance data as data associated with the exercise event.

20 Claims, 5 Drawing Sheets

Exercise A    202

| Metric Category 1 (e.g., step count) | Metric Category 2 (e.g., avg heart rate) | Metric Category 3 (e.g., caloric burn) |
|---|---|---|
| 9995 steps | 130 BPM | 200 kCal |

Exercise B    222

| Metric Category 1 (e.g., step count) | Metric Category 2 (e.g., avg heart rate) |
|---|---|
| 9940 steps | 128 BPM |

Exercise C    242

| Metric Category 1 (e.g., step count) |
|---|
| 9950 steps |

244
254

108

| | 304(1) | 304(2) | 304(3) | 304(4) | 304(5) | 304(6) |
|---|---|---|---|---|---|---|
| | **Metric Category 1 [Age]** | **Metric Category 2 [Gender]** | **Metric Category 3 [Step count]** | **Metric Category 4 [Avg. HR]** | **Metric Category 5 [Distance]** | **Metric Category 6 [Caloric Burn]** |
| 302(a)—A → | 31 | Male | 12000 steps | 135 | 6.1 miles | 600 kCal |
| 302(b)—B → | 27 | Female | 14000 steps | 142 | 7.3 miles | 750 kCal |
| 302(c)—C → | 25 | Male | 12500 steps | 150 | 6.3 miles | 670 kCal |
| 302(d)—D → | 35 | Female | 13500 steps | 160 | 6.9 miles | 740 kCal |

FIG. 3

TECHNIQUES FOR RETRIEVING PERFORMANCE DATA FROM AN EXERCISE DATABASE

TECHNICAL FIELD

The present disclosure relates to techniques for deriving exercise performance data of an individual from an exercise database.

BACKGROUND OF THE INVENTION

Consistent exercise has lasting health benefits. An exerciser's performance during a workout session depends on many factors including, for example, the exerciser's base line health status, nutritional habits, athletic skill, training regiment, etc. Such factors are the subject of much research. Often, an exerciser may wear one or more sensors to measure performance attributes of a workout. These sensors may record performance data for the individual to provide useful metrics to the user. An exerciser may wear the same sensors for multiple workouts or may wear different sensors for each workout instance.

BRIEF DESCRIPTION OF THE DRAWINGS

FIG. 3 shows an example exercise database maintained by the server displaying a plurality of exercise data entries.

DETAILED DESCRIPTION OF EXAMPLE EMBODIMENTS

Overview

Techniques are provided for retrieving performance data from an exercise database. At a server device, one or more exercise data entries are stored in a database. Each of the exercise data entries comprises one or more performance metrics for a corresponding metric category. The server receives first performance data of an individual performing an exercise event. The server selects one of the exercise entries in the database as a selected exercise entry. The server determines a metric category for the first performance data and matches the metric category of the first performance data with a same metric category for the selected exercise entry. The server retrieves second performance data from the selected exercise data entry, wherein the second performance data belongs to a metric category of the selected exercise data entry that does not match the metric category of the first performance data. The server assigns the second performance data as data associated with the exercise event.

Example Embodiments

The techniques described herein relate to retrieving performance data from an exercise database. A server may receive first performance data of an individual performing and exercise event, and based on the first performance data, the server may retrieve other performance data and associated it with the exercise event. This process allows the server to more efficiently and accurately assign performance data to an exercise event such that the server more accurately determines performance characteristics of an individual.

Figure 1:
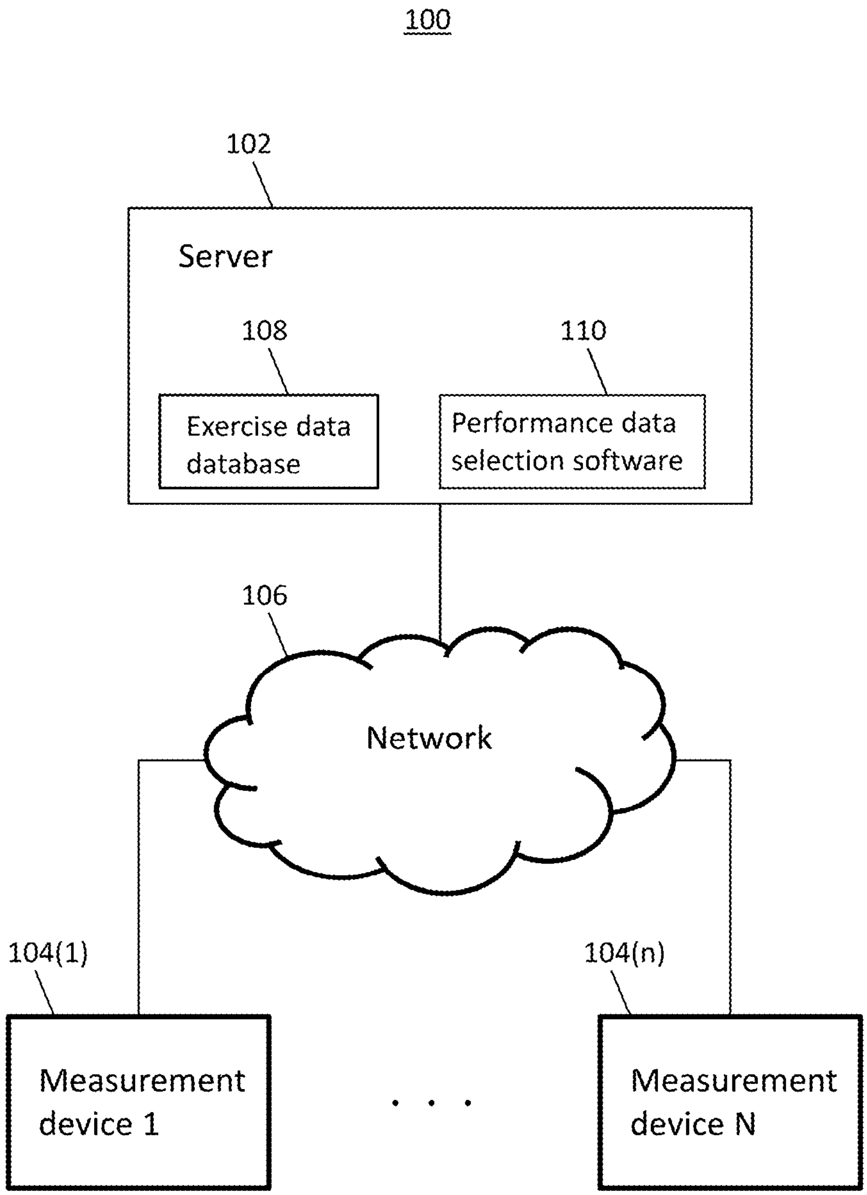
FIG. 1 shows an example system topology depicting a plurality of measurement devices configured to measure exercise performance data and a server configured to select appropriate performance data.

Reference is made to FIG. 1, which shows an example system topology 100 that includes a server 102 and a plurality of measurement devices 104(1)-**104(*n*). Measurement device 104(1) may be referred to herein as "measurement device 1," measurement device 104(2) may be referred to herein as "measurement device 2," and so on. The server 102 and the measurement devices 104(1)-104(*n*) are configured to communicate with each other over a network 106. The measurement devices 104(1)-104(*n*) are configured to communicate (e.g., via wired or wireless connection) with the server 102 via the network 106. These communications may be in accordance with known or heretofore contemplated wireless protocols (e.g., Wi-Fi, Bluetooth, radio frequency, near field communication, etc.). The measurement devices 104(1)-104(*n*) are configured to measure performance data of an individual (not shown in FIG. 1) performing an exercise event. For example, the measurement devices 104(1)-104(*n*) may be sensors worn by or affixed to the individual as the individual performs an exercise (or workout). The measurement devices 104(1)-104(*n*) may record data indicative of certain performance metrics during a workout and may send such data to the server 102. In one example, measurement device 104(1) may be a heart rate monitor configured to measure an individual's heart rate during an exercise, measurement device 104(2) may be a footwear sensor worn by the individual to measure his or her pace, distance and/or cadence during an exercise and measurement device 104(*n*)** may be a wrist worn wearable device configured to measure a user's step count. It should be appreciated that these are merely examples.

The measurement devices 104(1)-**104(*n*) send data to the server 102 via the network 106 (e.g., a Wide Area Network (WAN), Local Area Network (LAN), Personal Area Network (PAN), etc.). As described herein, the server 102 is a computing device that is configured to store in memory or be configured to access an exercise data database, represented in reference numeral 108 in FIG. 1. In one example, the exercise data database 108 may be stored in a memory component of the server 102, and in another example, the exercise data database may be stored remotely from the server 102 but accessible by the server 102**.

The server 102 also stores performance data selection software 110. As described herein, the performance data selection software 110 enables the server 102 to intelligently select one or more performance data entries in the exercise data database 108 to be associated with an exercise event performed by an individual. As will become apparent herein, the server 102 performs this selection based, in part, on performance data received from one or more of the measurement devices 104(1)-**104(*n*)**.

Figure 2A:
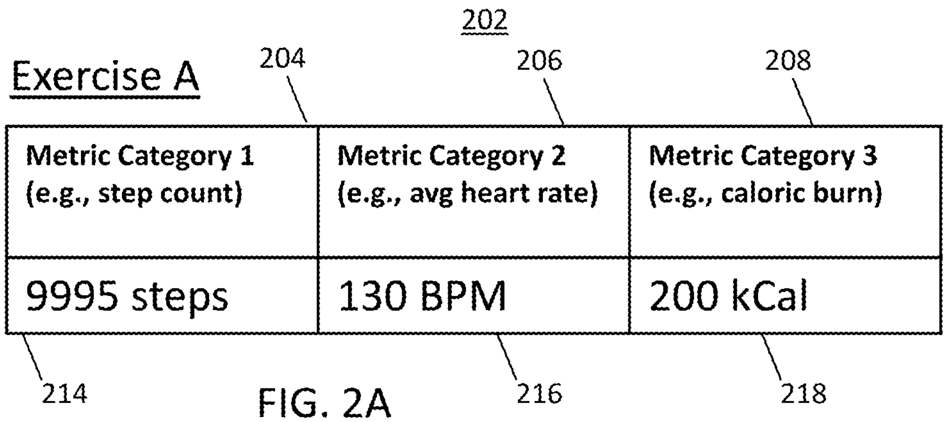
FIGS. 2A-2C show example performance data entries for multiple exercise workouts.
Figure 2B:
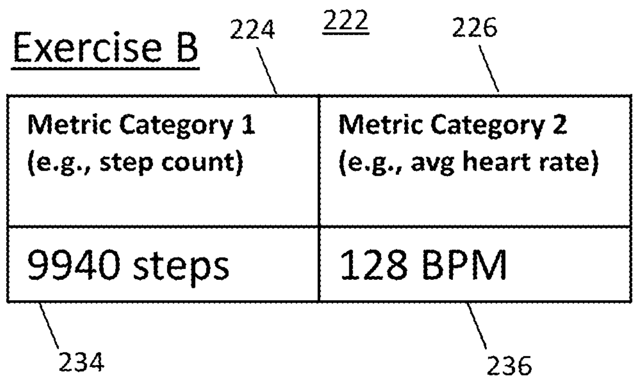
Figure 2C:
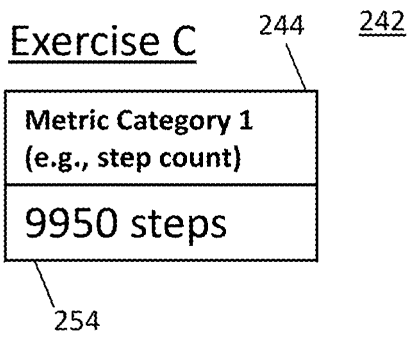

Reference is now made to FIGS. 2A-2C, which show example performance data entries in the exercise data database 108. In FIG. 2A, first performance data entry 202 has three metric categories. These categories are shown at reference numerals 204, 206 and 208. Non-limiting examples of the metric categories are shown in FIG. 2A with metric category 1 being a step count metric category, metric category 2 being an average heart rate metric category and metric category 3 being a caloric burn metric category. It should be appreciated that the categories are merely examples and that the metric categories may represent any data that is collected during physical activity. Examples of data collected during physical activity include activity data, physiological data, individual profile data (such as height, weight, age, gender, etc.), sleep data, nutritional data, etc. It should be appreciated that such data, and therefore entries in the exercise database, may be values derived from multiple other entries. For example, an entry in the exercise database may comprise caloric burn which may be derived from other entries in the exercise database such as average heart rate, exercise duration, age, height, weight, gender, etc. Non-limiting examples of metric categories include, but are not limited to, age, height, weight, body mass index, body fat percentage, heart rate, heart rate variability, caloric burn, pace, speed, cadence, stride length, distance traveled, sleep duration or any derived metric from any combination of these examples. For simplicity, FIGS. 2A-2C use step count as an example of metric category 1, average heart rate for metric category 2 and caloric burn for metric category 3.

As shown in FIG. 2A, the first performance data entry 202 has values stored for each of the metric categories. These values are shown at reference numerals 214, 216 and 218. That is, the value of 9995 steps is shown for the step count metric category, the value of 130 beats per minute (BPM) is shown for the average heart rate metric category and the value 200 kilocalories (kCal or "calories"). FIG. 2B shows a second performance data entry 222 with two metric categories 224 (step count) and 226 (average heart rate). The second performance data entry 222 has a value 9940 steps (shown at reference numeral 234) for the step count metric categories and a value of 128 BPM (shown at reference numeral 236) for the average heart rate metric value. FIG. 2C shows a third performance data entry 242 with one metric category 244 (step count) that has a value of 9950 steps (shown at reference numeral 254).

The performance data entries 202, 222 and 242 represent entries that were gathered over the course of different exercise events. Data of these entries may be received from the same individual for each of the different exercise events. Alternatively, at least one or more of the data entries 202, 222 and 242 may be from different individuals performing different exercise events. For example, data of the performance data entry 202 may be received (e.g., via one or more of the measurement devices 104(1)-104(*n*)) from a first individual, performance data entry 222 may be received from a second individual and performance data entry may be received from a third individual. As will become apparent hereinafter, in this example, the server 102 may assign to the third individual performance data that is found in the first performance data entry 202. For example, if the third individual has a profile (e.g., age, weight, height, gender, etc.) that is similar to the first individual, the server 202 may match the first metric category in performance data entry 242 with the first metric category in performance data entry 202 and may then assign to performance data entry 242 values 216 and 218 (associated with metric category 2 and metric category 3) to performance data entry 242. In other words, the server 102 may identify that there is a similar value in the first metric categories in both performance data entry 202 and 242, and thus may assign to performance data entry 242 data entry values that are not found in data entry 242 but that are found in data entry 202. These techniques will become apparent herein.

Reference is now made to FIG. 3. FIG. 3 shows an example of entries of the performance data database 108 ("database"). The database 108 shows multiple data entries 302(*a*)-302(*d*). Data entry 302(*a*) is shown at reference numeral "A" in FIG. 3, data entry 302(*b*) is shown at reference numeral "B, and so on. Each of the data entries 302(*a*)-302(*d*) is associated with a different individual performing an exercise event. The exercise events may also be different between the data entries 302(*a*)-302(*d*). Each of the data entries 302(*a*)-302(*d*) has data values for each of six metric categories, shown at reference numerals 304(1)-304(6) in FIG. 3. That is, in FIG. 3, each row of the database 108 may represent a data entry, and each column may represent a metric category. Metric category 1 is for an individual's age, metric category 2 is for an individual's gender, metric category 3 is for an individual's step count information, metric category 4 is for an individual's average heart rate (HR) during an exercise event, metric category 5 is for an individual's distance traveled during an exercise event and metric category 6 is for an individual's caloric burn during an exercise event. It should be appreciated that these metric categories are merely examples.

The database 108 is a dynamic database, and additional entries may be added to the database 108 as such data is received from an individual. Likewise, entries may be removed from the database 108, for example, based on recency and relevance. For example, the database 108 may grow to include other entries, some of which may not include values for all of the metric categories. In another example, the database 108 may grow to include other entries, some of which include values for additional metric categories not shown in FIG. 3. It should be appreciated that the database 108 may be stored on the server 102 or may be stored remote from the server 102 but accessible by it via, e.g., the network 106.

As stated above, the server 102 receives performance data of an individual performing an exercise event. This data may be from an individual who already has entries stored in the database 108, or it may be from a new individual. For example, the server 102 may receive performance data of an exercise event performed by an individual, and none of the individual's data may be previously stored in the database 108. Upon receiving the performance data, the server 102 may intelligently search the database 108 to select an analogous data entry that closely matches the performance data, and may assign values in the analogous data entry to the individual's exercise event. These values may include, for example, values that are not received by the server 102 for the current exercise event. In this example, the server 102 may receive information about an individual's step count during an exercise event, and the server 102 may retrieve an analogous data entry from the database 108 that closely matches the individual's step count value. From that analogous data entry, the server 102 may assign another value, such as caloric burn, to the individual's exercise event even though the server did not receive any caloric burn data from the individual performing the exercise event. Thus, the server 102 can intelligently mine and select data entries from the database 108 to assign to an individual's exercise event performance data in a metric category that is not received by the server 102 by the individual (via one or more of the monitoring devices 104(1)-104(*n*)) during the exercise event. As a result, an individual may not need to wear a sensor or other measurement device during an exercise event in order for the server 102 to obtain certain performance data. In an example, utilizing the techniques described herein, the server 102 can assign to an individual heart rate data for an exercise event even if the individual is not wearing a monitoring device that measures heart rate data.

The server 102 may also intelligently mine previous entries of the individual using the same or similar techniques described above.

The server 102 may search the database 108 to identify entries that are closely analogous to the performance data received by the pedometer. The server 102 may use several techniques to identify the closest matching entry in the database. For example, the server 102 may select the exercise data entry based on similar performance data. The server 102 may select the closet matching (e.g., matches the received data the closest) exercise data entry that represents performance data of a previous exercise event performed by the same individual. The server 102 may select the exercise event that is most recent in time to the exercise event of the individual (whether performed by the individual or performed by another individual). The server 102 may select the exercise entry performed by a person other than the individual who has similar physical characteristics of the individual. This selected exercise data entry may include similar performance data as that received by the server 102 for the individual from one or more of the monitoring devices 104(1)-104(*n*).

Take for example an individual who is male and 32 years old. Assume that the individual is wearing a pedometer and is performing a running exercise event. During or after the workout, the pedometer may send to the server 102 information about the individual's steps and distance traveled during the running workout, along with the individual's gender and age. For example, say the pedometer indicates that the individual has taken 12,000 steps and has traveled 6.4 miles. The server 102 may then use the processes described herein to select an appropriate analogous exercise entry in the database 108. The server 102 may select the analogous data entry based on one or more factors. For example, the server 102 may select past data of the individual stored in the database 108 (however, in FIG. 3, the individual does not have past data stored in the database 108). The server 108 may select the data entry that is closest to the individual's age. In FIG. 3, this entry is data entry A. Thus, in this example, the server 108 may assign data in metric categories other than age, gender, steps and distance to the individual based on this selection. In another example, the server 108 may select the data entry that more closely matches the step count data received from the pedometer. In this example, the step count data indicated 12,000 steps, and thus, the server 108 may select data entry A again, and may assign the average HR value (135 beats per minute) and caloric burn value (600 kCal) in data entry A to the running exercise performed by the individual.

In yet another example, the server 108 may select the data entry that more closely matches the distance traveled data received from the pedometer. Since the pedometer indicated a distance traveled of 6.4 miles by the individual during the running exercise event, the server 108 may select data entry C as the selected data entry since metric category 5 has the closest distance (6.3 miles) to the distance recorded by the pedometer. Thus, the server 108 may assign the average HR value (150 beats per minute) and caloric burn value (670 kCal) to the individual's running exercise event.

In another example, the server 102 may prioritize which data it utilizes to select the analogous data entry. For example, the server 102 may follow a metric hierarchy, where the highest priority metric category is used for data entry selection. If the highest priority metric category is not available or if the server 102 does not receive it, it may select the second highest priority, and so on. For example, the server 102 may select first the data entry that has the closest average heart rate, followed by the closest distance, the closest step count, the closest age and the closest gender. In another example, the server 102 may prioritize data that is received from the highest fidelity sensor. That is, the server 102 may select data entries that have data associated with metrics that are received via high fidelity sensors. In one example, a heart rate monitor may have a higher fidelity hierarchy than a pedometer. Thus, the server 102 may select data entries based on the closest match to the higher fidelity heart rate entry over the lower fidelity pedometer entry. It should be appreciated that these are merely examples, and the server 102 may follow more complex hierarchies that involve multiple metrics.

Figure 4:
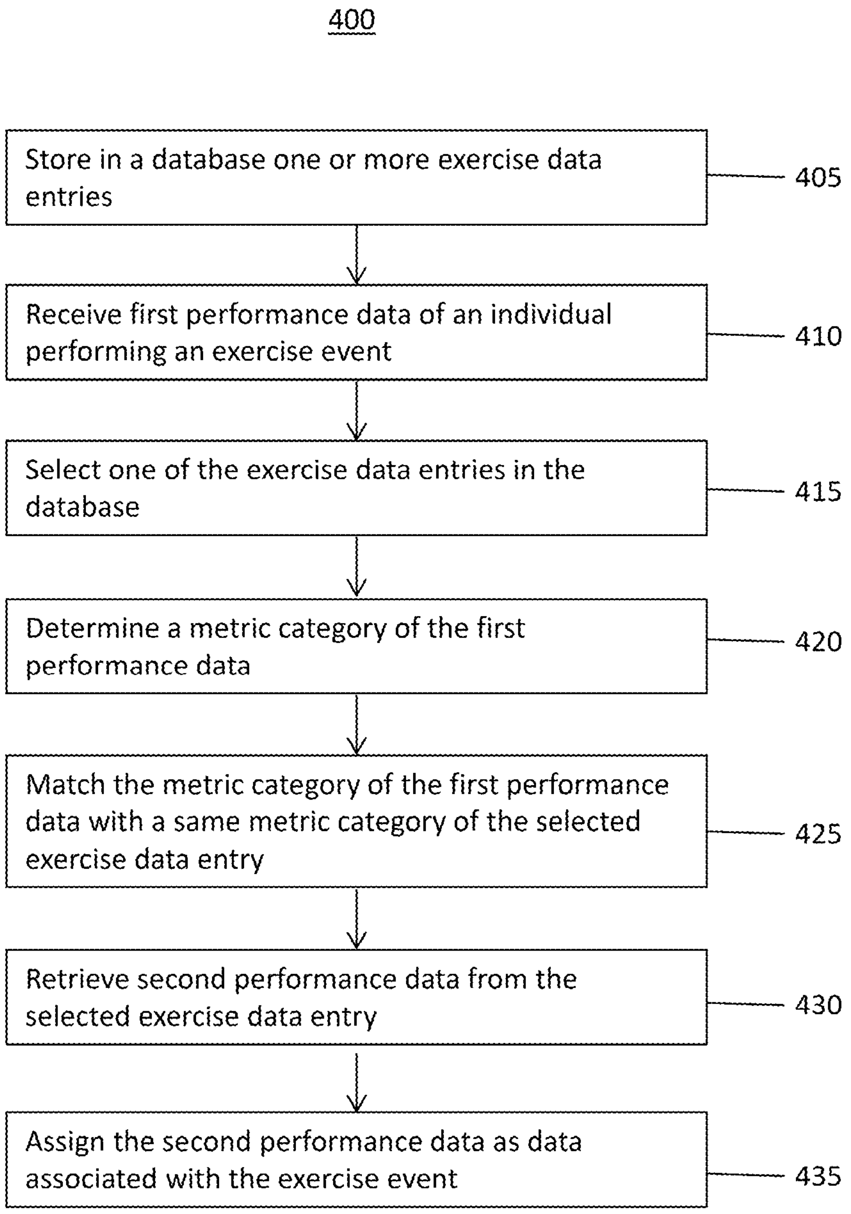
FIG. 4 shows an example flow chart depicting operations for selecting appropriate performance data.

Reference is now made to FIG. 4, which shows an example flow chart 400 that depicts operations for selecting performance data. At 405, the server 102 stores in a database one or more exercise entries. The server 102 then receives first performance data of an individual performing an exercise event, as shown at reference numeral 410. The server 102 may receive the first performance data from one or more of the monitoring devices 104(1)-104(*n*), as described above. At 415, the server 102 selects one of the exercise data entries in the database 108 as the selected (or analogous) data entry. At 420, the server 102 determines a metric category of the first performance data, and at reference numeral 425, the server 102 matches the metric category of the first performance data with a same metric category of the selected exercise data entry. The server 102 then retrieves second performance data from the selected exercise data entry, as shown at operation 430. The second performance data, for example, belongs to a metric category of the selected exercise data entry that does not match the metric category of the first performance data. At operation 435, the server 102 assigns the second performance data as data associated with the exercise event.

Figure 5:
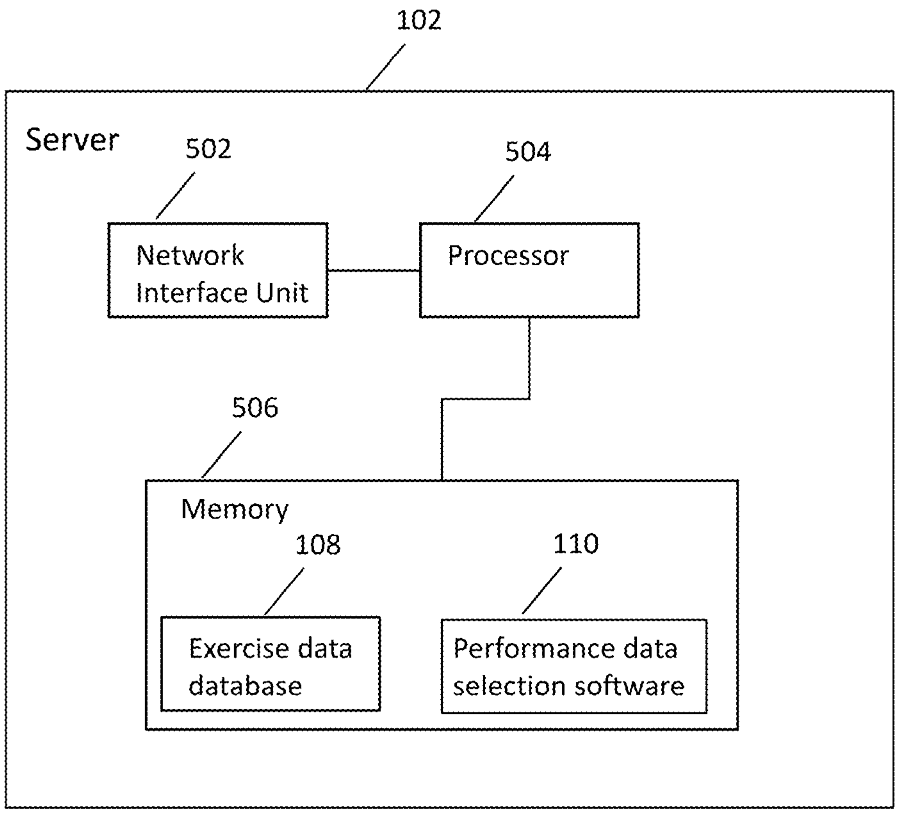
FIG. 5 shows an example block diagram of the server that selects performance data from the exercise database.

Reference is now made to FIG. 5 which shows an example block diagram of the server 102. As stated above, in general, the server 102 intelligently and efficiently selects performance data from the exercise database 108. The server 102 has a network interface unit 502, a processor 504 and a memory 506. The network interface unit 502 is configured to send and receive data (e.g., performance data from one or more of the monitoring devices 104(1)-104(*n*)) via the network 106. The network interface unit is connected to the processor 504. The processor 504 is, for example, a microprocessor or microcontroller that is configured to execute program logic instructions (i.e., software) for carrying out various operations and tasks of the server 104, as described above. For example, the processor 504 is configured to execute the performance data selection software 110 stored in memory 506 to intelligently select appropriate data entries from the exercise data database 108, as described above. The functions of the processor 504 may be implemented by logic encoded in one or more tangible computer readable storage media or devices (e.g., storage devices, compact discs, digital video discs, flash memory drives, etc. and embedded logic such as an application specific integrated circuit (ASIC), digital signal processor instructions, software that is executed by a processor, etc.).

The memory 506 may comprise read only memory (ROM), random access memory (RAM), magnetic disk storage media devices, optical storage media devices, flash memory devices, electrical, optical, or other physical/tangible (non-transitory) memory storage devices. The memory 506 stores software instructions for the performance data selection software 110. Thus, in general, the memory 506 may comprise one or more computer readable storage media (e.g., a memory storage device) encoded with software comprising computer executable instructions and when the software is executed (e.g., by the processor 504) it is operable to perform the operations described for the performance data selection software 110, as described herein. The memory also stores the exercise data database 108.

The performance data selection software 110 may take any of a variety of forms, so as to be encoded in one or more tangible computer readable memory media or storage device for execution, such as a fixed logic or programmable logic (e.g., software/computer instructions executed by a processor), and the processor 504 may be an ASIC that comprises fixed digital logic or a combination thereof.

For example, the processor 504 may be embodied by digital logic gates in a fixed or programmable digital logic integrated circuit, which digital logic gates are configured to perform the performance data selection software 110. In general, the performance data selection software 110 may be embodied in one or more computer readable storage media encoded with software comprising computer executable instructions and when the software is executed operable to perform the operations described herein.

In summary, a method is provided comprising: at a server device, storing in a database one or more exercise data entries, wherein each one of the exercise data entries comprises one or more performance metrics for a corresponding metric category; receiving first performance data of an individual performing an exercise event; selecting one of the exercise data entries in the database; determining a metric category of the first performance data; matching the metric category of the first performance data with a same metric category of the selected exercise data entry; retrieving second performance data from the selected exercise data entry, wherein the second performance data belongs to a metric category of the selected exercise data entry that does not match the metric category of the first performance data; and assigning the second performance data as data associated with the exercise event.

In addition, one or more computer readable storage media is provided that is encoded with software comprising computer executable instructions and when the software is executed operable to: store in a database maintained by a server one or more exercise data entries, wherein each one of the exercise data entries comprises one or more performance metrics for a corresponding metric category; receive first performance data of an individual performing an exercise event; select one of the exercise data entries in the database; determine a metric category of the first performance data; match the metric category of the first performance data with a same metric category of the selected exercise data entry; retrieve second performance data from the selected exercise data entry, wherein the second performance data belongs to a metric category of the selected exercise data entry that does not match the metric category of the first performance data; and assign the second performance data as data associated with the exercise event.

The above description is intended by way of example only. Various modifications and structural changes may be made therein without departing from the scope of the concepts described herein and within the scope and range of equivalents of the claims.

What is claimed is:

1. A method of growing an incomplete database in an activity tracking system, the method comprising:

at a server device, storing in a database one or more exercise data entries, wherein each one of the exercise data entries comprises one or more performance metrics for a corresponding metric category;

at a sensor device carried by an individual performing a first exercise event, sensing first performance data of the individual;

electronically transmitting, by the sensor device, the first performance data to the server device;

at the server device, receiving the electronic transmission of the first performance data of the individual;

creating a first data entry including the first performance data in the database;

selecting one of the exercise data entries in the database other than the first data entry, wherein the selected exercise data entry does not include the first performance data;

determining a metric category of the first performance data, wherein determining a metric category of the first performance data comprises selecting a highest priority metric category in a metric hierarchy for the first performance data;

matching the determined metric category of the first performance data with a same metric category of the selected exercise data entry;

identifying the selected one of the exercise data entries as an analogous data entry;

retrieving second performance data from the analogous data entry, wherein the second performance data belongs to a metric category of the analogous data entry that does not match the metric category of the first performance data; and automatically amending the first data entry by assigning the second performance data from the analogous data entry as additional data included in the first data entry and associated with the first exercise event, and thereby growing the database to include additional data in the first data entry that does not match the metric category of the first performance data.

2. The method of claim 1, wherein selecting comprises selecting the one of the exercise data entries based on information of the individual stored in the database, wherein the analogous data entry is an exercise data entry of a previous exercise event performed by the individual with similar performance data as the first performance data.

3. The method of claim 1, wherein selecting comprises selecting an exercise data entry that represents performance data of a previous exercise event with similar performance data as the first performance data.

4. The method of claim 3, wherein selecting the exercise data entry of the previous exercise event comprises selecting the exercise data entry of the previous exercise event that is most recent in time to the first exercise event.

5. The method of claim 4, wherein selecting the exercise data entry of the previous exercise event that is most recent in time further comprises selecting the exercise data entry of the previous exercise event performed by the individual.

6. The method of claim 1, wherein the individual performing the first exercise event is a first individual having physical characteristic data stored in the database, wherein the analogous data entry is an exercise data entry of a previous exercise event performed by a second individual other than the first individual, the second individual having physical characteristic data stored in the database that is similar to the physical characteristic data of the first individual, and further wherein the analogous data entry has similar performance data as the first performance data.

7. The method of claim 1, wherein storing comprises storing in the database exercise data entries that comprise performance metrics in at least one or more of the metric categories: age, height, weight, body mass index, body fat percentage, heart rate, heart rate variability, caloric burn, pace, speed, cadence, stride length, distance traveled or sleep duration or a derived metric including one or more of a combination of heart rate, heart rate variability, caloric burn, pace, speed, cadence, stride length, distance traveled or sleep duration.

8. The method of claim 1, wherein the sensor device is affixed to or worn by the individual during the first exercise event.

9. The method of claim 1, wherein assigning comprises assigning the second performance data as data associated with the first exercise event such that the individual does not have to wear a second sensor device configured to measure the second performance data during the first exercise event.

10. The method of claim 1, wherein assigning comprises assigning the second performance data as data associated with the first exercise event when the server does not receive during the first exercise event any performance data in a same metric category as the second performance data.

11. One or more non-transitory computer readable storage media encoded with software comprising computer executable instructions and when the software is executed operable to:

store in a database maintained by a server one or more exercise data entries, wherein each one of the exercise data entries comprises one or more performance metrics for a corresponding metric category;

cause a remote sensor device to electronically transmit first performance data of an individual performing a first exercise event;

receive the first performance data from the remote sensor device that electronically transmitted the first performance data, wherein the first performance data is data associated with the first exercise event and the first exercise event was performed by the individual while carrying the remote sensor device;

create a first data entry including the first performance data in the database;

select one of the exercise data entries other than the first data entry from the database such that the selected exercise data entry does not include the first performance data;

determine a metric category of the first performance data, wherein determining a metric category of the first performance data comprises selecting a highest priority metric category in a metric hierarchy for the first performance data;

match the determined metric category of the first performance data with a same metric category of the selected exercise data entry;

identify the selected one of the exercise data entries as an analogous data entry;

retrieve second performance data from the analogous data entry, wherein the second performance data belongs to a metric category of the analogous data entry that does not match the metric category of the first performance data; and amend the first data entry by assigning the second performance data from the analogous data entry as additional data included in the first data entry and associated with the first exercise event such that the database grows to include additional data in the first data entry that does not match the metric category of the first performance data.

12. The computer readable storage media of claim 11, wherein the instructions operable to select comprise instructions operable to select the one of the exercise data entries based on information of the individual stored in the database, wherein the analogous data entry is an exercise data entry of a previous exercise event performed by the individual with similar performance data as the first performance data.

13. The computer readable storage media of claim 11, wherein the instructions operable to select comprise instructions operable to select an exercise data entry that represents performance data of a previous exercise event with similar performance data as the first performance data.

14. The computer readable storage media of claim 13, wherein the instructions operable to select the exercise data entry of the previous exercise event comprise instructions operable to select the exercise data entry of the previous exercise event that is most recent in time to the first exercise event.

15. The computer readable storage media of claim 14, wherein the instructions operable to select the exercise data entry of the previous event that is most recent in time further comprise instructions operable to select the exercise data entry of the previous exercise event performed by the individual.

16. The computer readable storage media of claim 11, wherein the individual performing the first exercise event is a first individual having physical characteristic data stored in the database, wherein the analogous data entry is an exercise data entry of a previous exercise event performed by a second individual other than the first individual, the second individual having physical characteristic data stored in the database that is similar to the physical characteristic data of the first individual, and further wherein the analogous data entry has similar performance data as the first performance data.

17. The computer readable storage media of claim 11, wherein the instructions operable to store comprise instructions operable to store exercise data entries that comprise performance metrics in at least one or more of the metric categories: age, height, weight, body mass index, body fat percentage, heart rate, heart rate variability, caloric burn, pace, speed, cadence, stride length, distance traveled or sleep duration or a derived metric including one or more of a combination of heart rate, heart rate variability, caloric burn, pace, speed, cadence, stride length, distance traveled or sleep duration.

18. The computer readable storage media of claim 11, wherein the remote sensor device is affixed to or worn by the individual during the first exercise event.

19. The computer readable storage media of claim 11, wherein the instructions operable to assign comprise instructions operable to assign the second performance data as data associated with the exercise event such that the individual does not have to wear a second sensor device configured to measure the second performance data during the first exercise event.

20. The computer readable storage media of claim 11, wherein the instructions operable to assign comprise instructions operable to assign the second performance data as data associated with the first exercise event when the server does not receive during the first exercise event any performance data in a same metric category as the second performance data.

* * * * *